(12) United States Patent
Nelson et al.

(10) Patent No.: US 9,067,014 B2
(45) Date of Patent: Jun. 30, 2015

(54) ATTACHMENT DEVICE FOR IDENTIFYING CONSTITUENTS WITHIN A FLUID

(75) Inventors: Elizabeth Nelson, Newton, MA (US); Karthik Ranganathan, Edgewater, NJ (US); Bart D. Peterson, Farmington, UT (US); William R. Marshall, Sandy, UT (US); David Feygin, Glen Rock, NJ (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 283 days.

(21) Appl. No.: 13/410,077

(22) Filed: Mar. 1, 2012

(65) Prior Publication Data

US 2012/0222468 A1 Sep. 6, 2012

Related U.S. Application Data

(60) Provisional application No. 61/449,314, filed on Mar. 4, 2011, provisional application No. 61/450,204, filed on Mar. 8, 2011, provisional application No. 61/449,263, filed on Mar. 4, 2011, provisional application No. 61/450,198, filed on Mar. 8, 2011.

(51) Int. Cl.
*G01N 33/00* (2006.01)
*A61M 5/168* (2006.01)
*G06F 19/00* (2011.01)

(52) U.S. Cl.
CPC .............. *A61M 5/168* (2013.01); *G06F 19/34* (2013.01); *G06F 19/3468* (2013.01)

(58) Field of Classification Search
CPC ..... A61M 5/168; G06F 19/34; G06F 19/3468
USPC ............ 73/53.01, 61.41, 61.43, 61.44, 61.71, 73/64.56; 702/23, 25
See application file for complete search history.

(56) References Cited

U.S. PATENT DOCUMENTS

| | | | | |
|---|---|---|---|---|
| 3,631,437 A | * | 12/1971 | Campbell et al. | 340/521 |
| 4,607,671 A | * | 8/1986 | Aalto et al. | 141/329 |
| 4,759,756 A | * | 7/1988 | Forman et al. | 604/413 |
| 4,846,005 A | * | 7/1989 | Bacehowski et al. | 73/864.81 |
| 5,046,496 A | * | 9/1991 | Betts et al. | 600/352 |
| 5,145,565 A | * | 9/1992 | Kater et al. | 600/341 |
| 5,301,543 A | | 4/1994 | Reichert | |
| 5,390,671 A | * | 2/1995 | Lord et al. | 600/347 |
| 5,563,584 A | * | 10/1996 | Rader et al. | 340/618 |

(Continued)

FOREIGN PATENT DOCUMENTS

| EP | 1 739 585 A2 | 1/2007 |
|---|---|---|
| WO | WO 02/096781 A1 | 12/2002 |

(Continued)

*Primary Examiner* — Peter Macchiarolo
*Assistant Examiner* — Natalie Huls
(74) *Attorney, Agent, or Firm* — Jeanne Lukasavage; Craig Metcalf; Kirton McConkie (57) ABSTRACT

An attachment device for identifying one or more constituents within a fluid includes a first end configured to selectively attach to an opening of a container holding a fluid, and a sensor coupled to the attachment body. The sensor further includes one or more sensor elements positioned to detect and analyze a fluid within the container. The sensor is further configured to perform one or more tests on the fluid, wherein the one or more tests are useful in identifying one or more constituents within the fluid.

17 Claims, 8 Drawing Sheets

(56) References Cited

U.S. PATENT DOCUMENTS

| | | | |
|---|---|---|---|
| 5,620,008 A * | 4/1997 | Shinar et al. | 600/576 |
| 6,193,675 B1 * | 2/2001 | Kraus et al. | 600/576 |
| 6,264,611 B1 * | 7/2001 | Ishikawa et al. | 600/486 |
| 6,753,186 B2 | 6/2004 | Moskoff | |
| 6,758,835 B2 * | 7/2004 | Close et al. | 604/272 |
| 7,553,028 B2 | 6/2009 | Engle et al. | |
| 7,811,279 B2 | 10/2010 | John | |
| 8,038,657 B2 * | 10/2011 | Davis et al. | 604/253 |
| 8,287,073 B2 | 10/2012 | Schippers | |
| 2003/0100861 A1 * | 5/2003 | Bergeron et al. | 604/116 |
| 2004/0171983 A1 * | 9/2004 | Sparks et al. | 604/65 |
| 2006/0253297 A1 | 11/2006 | Mallett et al. | |
| 2007/0100518 A1 | 5/2007 | Cooper | |
| 2007/0135779 A1 | 6/2007 | Lalomia et al. | |
| 2007/0179448 A1 * | 8/2007 | Lim et al. | 604/187 |
| 2007/0191700 A1 | 8/2007 | Say et al. | |
| 2008/0129475 A1 | 6/2008 | Breed et al. | |
| 2008/0169044 A1 | 7/2008 | Osborne et al. | |
| 2008/0237092 A1 | 10/2008 | Mallett et al. | |
| 2008/0319795 A1 | 12/2008 | Poteet et al. | |
| 2009/0036764 A1 * | 2/2009 | Rivas et al. | 600/365 |
| 2009/0216205 A1 | 8/2009 | Ryan et al. | |
| 2009/0275815 A1 * | 11/2009 | Bickoff et al. | 600/345 |
| 2010/0145274 A1 * | 6/2010 | Royce | 604/132 |
| 2010/0191084 A1 * | 7/2010 | Shah et al. | 600/347 |
| 2010/0280486 A1 | 11/2010 | Khair et al. | |
| 2010/0305499 A1 | 12/2010 | Matsiev et al. | |
| 2011/0009817 A1 * | 1/2011 | Bennett et al. | 604/93.01 |
| 2011/0015583 A1 * | 1/2011 | Davis et al. | 604/253 |
| 2011/0060198 A1 | 3/2011 | Bennett et al. | |
| 2011/0060229 A1 * | 3/2011 | Hulvershorn et al. | 600/486 |
| 2011/0112474 A1 * | 5/2011 | Bochenko et al. | 604/68 |
| 2011/0144530 A1 * | 6/2011 | Felder | 600/561 |
| 2011/0264069 A1 * | 10/2011 | Bochenko | 604/404 |
| 2011/0270027 A1 * | 11/2011 | Augarten et al. | 600/37 |
| 2012/0016345 A1 * | 1/2012 | Carter et al. | 604/533 |
| 2012/0065617 A1 | 3/2012 | Matsiev et al. | |
| 2013/0177455 A1 * | 7/2013 | Kamen et al. | 417/313 |
| 2013/0226137 A1 * | 8/2013 | Brown | 604/503 |

FOREIGN PATENT DOCUMENTS

| | | |
|---|---|---|
| WO | WO 2004/033003 A1 | 4/2004 |
| WO | WO 2004/095379 A1 | 11/2004 |
| WO | WO 2009/114115 A1 | 9/2009 |

* cited by examiner

ATTACHMENT DEVICE FOR IDENTIFYING CONSTITUENTS WITHIN A FLUID

RELATED APPLICATIONS

This application claims the benefit of U.S. Provisional Application No. 61/449,314 filed Mar. 4, 2011, entitled SMART DELIVERY CONTAINER, U.S. Provisional Application No. 61/450,204 filed Mar. 8, 2011, entitled SMART DRUG CONTAINER ATTACHMENT, U.S. Provisional Application No. 61/449,263 filed Mar. 4, 2011, entitled SMART CLOSED LOOP MEDICATION ADMINISTRATION, and U.S. Provisional Application No. 61/450,198 filed Mar. 8, 2011, entitled SMART WASTE DISPOSAL, each of which is incorporated herein by reference in their entirety.

BACKGROUND OF THE INVENTION

Each year, harmful medication errors involving injectable drugs cause many preventable adverse drug events. These medication errors include errors caused by the incorrect preparation of liquid medications, such as intravenous (IV) medications and liquid oral medications (herein referred to simply as "fluid" or "IV fluid"). For example, fluids can be incorrectly prepared when made with an incorrect drug, when prepared with an incorrect drug dose or drug concentration, or when prepared with expired or contaminated drugs. Such errors can be difficult, expensive, or impossible for pharmacists, caregivers, or care facilities to detect. For these reasons, drug preparation errors frequently go undetected.

After being prepared, a fluid is placed in a container, such as an IV bag or syringe. The container can be labeled with the identity of the fluid and drugs within the fluid. When the fluid is delivered to caregivers for administration to a patient, the caregiver checks the label to verify the correct identity of the fluid. If the label indicates the correct fluid, the caregiver administers the fluid. However, the caregiver generally has no way to verify that the label accurately identifies the fluid.

In light of the high number of drug preparation errors that occur despite current practices, it would be beneficial to develop systems and methods to reduce the occurrence of adverse drug events caused by incorrect drug preparation.

BRIEF SUMMARY OF THE INVENTION

The present invention has been developed in response to problems and needs in the art that have not yet been fully resolved by currently available systems and methods. Thus, these systems and methods are developed to enable the identification and verification of a fluid containing one or more drugs after the fluid is prepared. The systems and methods of the present invention are further developed to enable identification and verification of fluids which do not contain drugs, but which identification is still beneficial. Such systems and methods can identify one or more of the contents and/or the characteristics of a fluid (also referred to herein simply as "identify the fluid") to ensure that it was properly prepared or is properly labeled. Using these systems and methods, pharmacists and caregivers can have a higher likelihood of detecting drug preparation errors before the drug is administered to a patient.

Accordingly, the present systems can include an attachment device that attaches to an opening in a container of fluid and tests a fluid within the container. The attachment device includes a sensor that has one or more sensor elements positioned so that they contact a fluid flowing through the attachment device when the attachment device is connected to a container containing a fluid. In some implementations, a sensor is provided in proximity to a fluid, wherein the sensor is capable of detecting and/or analyzing the fluid without contacting the fluid. For example, the sensor may include an optical sensor, such as a photodiode, an image sensor, a thermographic camera, or an optical fiber connection. The sensor is configured to perform one or more tests on the fluid, wherein the one or more tests are useful in identifying the fluid and/or a constituent of the fluid.

As used herein, the term "identifying a fluid" refers to process or method by which the identity, contents or properties of a fluid are identified and made available to a user. Identifying a fluid can include identifying one or more drug constituents within a fluid. Identifying a fluid can also include identifying one or more other contents and/or characteristics of the fluid, such as a concentration, a flow measurement, a dose, and/or a degradation (e.g., expiration or contamination) of the one or more constituents of the fluid.

An attachment device in accordance with the present invention may include various configurations. For example, in some implementations an attachment device includes a spike for attaching to an IV bag. In other implementations, an attachment device comprises a cap, a stopper, a vial, a luer connector, or some other device capable of being connected to a container. In some implementations, an attachment device is provided that is configured to attach to a variety of containers. For example, an attachment device is provided that is configured to attach to an IV bag, a syringe, and ampule, and a vial. In some configurations, the attachment body has a first end having an attachment feature that attaches to an opening or other surface of a container. The attachment device may also have an internal chamber in which a fluid may be temporarily stored. The internal chamber may also open to the first end or second end and have a sensor element disposed therein to contact and test fluid within the internal chamber. In some implementations, an attachment device further includes an expansion chamber that facilitates fluid entry, but does not allow the fluid to contact an external environment.

The sensor may further have one or more contact surfaces that are externally accessible from the attachment device. In some implementations, a vent membrane is disposed between the internal chamber and an exterior environment to facilitate fluid entry into the internal chamber, wherein the vent membrane permits passage of air but is impermeable to liquids, such as blood. In some implementations, the attachment body also includes a spike that extends from its first end and forms a fluid path into the internal chamber. In some instances, a separate adapter unit is provided to permit compatible coupling of the attachment device to one or more different types of containers.

The systems of the present invention may further include a display unit that is connected to a processor unit for displaying information provided by the processor unit. The systems of the present invention may also be configured to access and update an electronic medical record (EMR) system with information provided by the processor unit. For example, in some implementations the processor unit accesses information from a medication order recorded on the EMR system and then compares the identity of the ordered fluid to an identity of a fluid in a container, as determined by a system of the present invention. The processor unit may then provide an alert were the processor unit detects a discrepancy between the two identities. The system can also be electronically coupled to a printer or RFID programmer.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following, more detailed description, as represented in the figures, is not intended to limit the scope of the invention as claimed, but is merely representative of presently preferred embodiments of the invention.

The figures show some various representative embodiments of systems and methods of identifying a fluid within a container. The system may identify a fluid and then communicate its identity to a computer system, a pharmacist, and/or a caregiver, in order to detect and reduce the occurrence of drug preparation errors. The system and method may further be used in pharmacies and other facilities where liquids containing drugs (substances intended for use in the diagnosis, cure, mitigation, treatment, or prevention of a disease) are prepared or administered. The use of the system can thus enable pharmacists and caregivers to identify a fluid without sending the fluid to a laboratory for testing and identification. The system may also provide real-time identification of fluids which can facilitate a caregiver in identifying preparation errors. The system may further record the identity of the fluid on a record system which may be used to prepare an accurate label that can be placed on the container.

Figure 1:
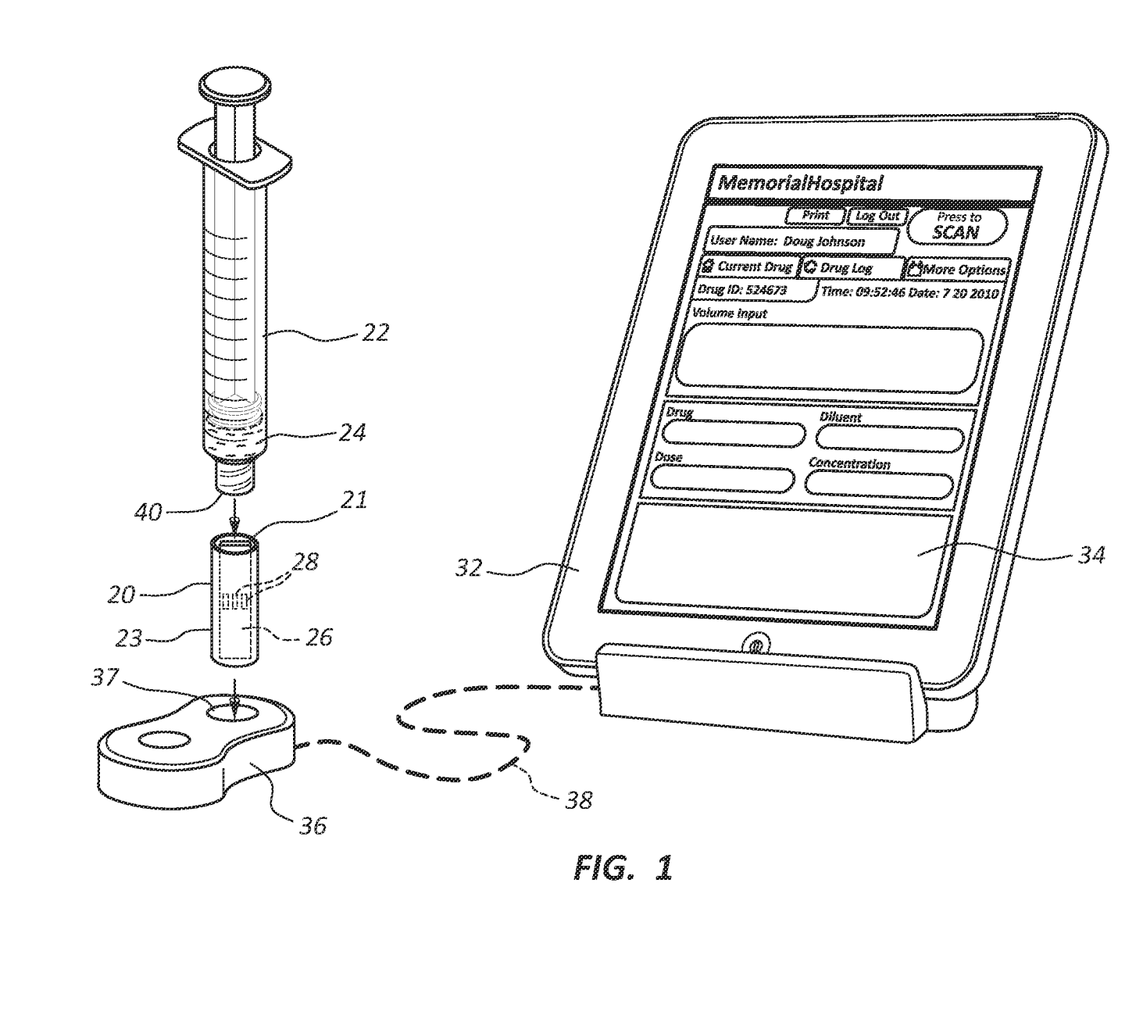
FIG. 1 is a perspective view of a system for identifying one or more constituents within a fluid in accordance with a representative embodiment of the present invention.

Reference will now be made to FIG. 1, which illustrates an attachment device 20 that is configured to identify a fluid 24 within a container 22. In some embodiments, attachment device 20 comprises a sensor 26 that is configured to perform tests on fluid 24 to identify one or more parameters, constituents, or characteristics of fluid 24. In some embodiments, attachment device 20 comprises a surface to facilitate attachment of attachment device 20 to a container 22. Attachment device 20 further comprises a second surface to facilitate attachment of attachment device 20 to a receiving unit 36. Specific structures related to attachment device 20 and receiving unit 36 will be discussed below.

Attachment device 20 as described herein is used to identify a fluid. As used herein, the term "identifying the fluid" refers to the process or method of identifying at least one or more of the constituents, properties, characteristics or parameters of a fluid 24. For example, the process of identifying a fluid 24 may include identifying at least one or more drugs within a fluid 24. Identifying the fluid 24 may also include identifying one or more other constituents and/or characteristics of the fluid 24, such as a concentration, a dose, or a degradation (e.g., expiration or contamination) of the one or more constituents in the fluid 24. The process of identifying a fluid 24 may further include identifying a fluid that does not contain a drug, but for which an accurate identification is beneficial (e.g., such as identifying a saline solution). Attachment device 20 may be configured to selectively attach to an opening 40 in a container 22 of fluid 24. The attachment device 20 can be in the form of a cap, a stopper, a vial, or a luer connector (such as the Q-Syte™ connector from Becton, Dickinson and Company).

As mentioned, the attachment device 20 comprises a sensor 26 that is configured to perform one or more tests on fluid 24. Attachment device 20 is further coupled to a processor unit 32 which is configured to receive and analyze sensor measurements or data from sensor 26. Processor unit 32 may further comprise computer executable instructions for receiving and analyzing sensor measurements or data from sensor 26. Once the identity or other characteristic of fluid 24 is determined, processor unit 32 displays said information on a display device 34.

The combined sensor 26 and processor unit 32 can be referred to as a fluid identification system 30. Fluid identification system 30 may include various configurations, which will be described in detail below. Various examples of sensors suitable for implementation in the present invention are disclosed in International Application No. WO 2009/114115, published Sep. 17, 2009, which is incorporated herein by reference, in its entirety.

With further reference to FIG. 1, a sensor 26 may include one or more sensor elements 28. Sensor element 28 is configured to detect or otherwise test various characteristics of fluid 24. In some embodiments, the sensor element 28 comprises a sensing surface adapted for interaction with and being responsive to the fluid 24 within the container 22. In some instances, the one or more sensor elements 28 are positioned such that they interact with fluid 24. In some embodiments, the one or more sensor elements 28 are one or more electrodes. The sensor elements 28 and/or the sensor 26 can incorporate a semiconductor device that may be mounted on a printed circuit board or another substrate.

The sensor 26 can be configured to sense one or more parameters or characteristics of fluid 24 within container 22 by performing one or more tests on the fluid 24. Parameters of the fluid 24 include any of a set of physical properties whose values determine a characteristic or behavior of the fluid (e.g. temperature, density, impedance, pressure, viscosity, etc.). Data resulting from the tests performed by sensor 26 can be referred to as sensor measurements or data which can be transmitted to a processor unit 32 that is configured to identify one or more characteristics, perimeters or constituents within the fluid based on these sensor measurements.

For example, in some embodiments, the sensor 26 can be configured to sense the impedance of the fluid 24. As such, an electrical signal can be driven through the one or more sensor elements 28 into the fluid 24 at a range of frequencies. The sensor elements 28 can subsequently measure the current generated in the fluid by the electrical signal. The electrical signal is then sent to processor unit 32 as sensor measurements. The sensor measurements can then be conditioned and/or and processed by processor unit 32. The sensor measurements, which can include measured current and transmitted voltages, and are then used to form frequency dependent maps of the impedance of the fluid 24. The maps, or signatures, may be unique to each fluid 24 containing a drug, given it concentration, purity, and state of degradation. The signatures can then be compared to a library of pre-loaded signatures, the comparison of which is used to identify the fluid 24. In some configurations, sensor 26 uses one or more alternative or additional sensing methods to sense one or more parameters of the fluid 24.

Fluid identification system 30 may further use a multi-parametric approach to identify drugs within a fluid 24. In such an approach multiple parameters can be sensed (e.g., refractive index, electrochemical potential, impedance, admittance, and conductivity). This multi-parametric approach is referred to as multiplexing. Hence, a fluid 24 can be sensed with multiple sensors 26, or with a sensor 26 having multiple sensor elements 28. Fluid 24 may further be sensed with a single sensor element 28 using multiplexing to obtain independent sensor measurements. Thus, the sensor measurements can generate a multi-parametric profile for fluid 24.

Reference will now be made more particularly to the processor unit 32 of FIG. 1. As mentioned, the processor unit 32 can be configured to receive sensor measurements from the sensor 26 and use those sensor measurements to identify the fluid 24. Accordingly, processor unit 32 communicates with the sensor 26 via a communication link 38. In some embodiments, processor unit 32 further powers sensor 26. For example, in some embodiments processor unit 32 is electronically coupled to the sensor 26 whereby processor unit 32 powers sensor 26 two enable it to perform tests on fluid 24. During the process of testing or upon completion of these tests, the processor unit 32 can receive sensor measurements from the sensor 26.

Processor unit 32 may further include a computer system, in which some or all of the processing logic can be implemented for identifying a fluid using the sensor measurements. The computer system can include a general-purpose or special-purpose processing subsystem. For example, the computer system can be a personal computer, a notebook computer, a tablet computer, a workstation, a minicomputer, a mainframe, a supercomputer, a multi-processor system, a mobile electronic device (e.g. a mobile cellular phone), a processor-based electronic device, or the like, which is coupled to the other components of processor unit 32. Additionally, processor unit 32 may be incorporated into a computer system used in care facilities, such as a smart pump, an automated dispensing cabinet (ADC), a bedside computer system, a personal computer, a thin client, or other suitable computer system.

In some embodiments, computer-executable instructions are provided having instructions to cause a processor of the computer system to execute functions for implementing logical operations. The computer-executable instructions can be permanently stored in the instruction memory of the computer system, or be temporarily loaded and stored into the instruction memory of the computer system from a computer-readable medium. The computer-executable instructions can include data structures, objects, programs, routines, or other program modules that can be accessed by the processor.

In some embodiments, a computer system of the processor unit 32 is used to implement a process for identifying fluid 24 based on sensor measurements. In some embodiments, one or more software modules are provided having instructions to cause the processor to implement these modules. Processor unit 32 may also be used to implement a process for processing, storing, displaying or transmitting data relating to the identification of the fluid 24.

Processor unit 32 may further be electronically coupled to a display device 34 is configured to display the identification of fluid 24 and/or other desired information. Display device 34 thereby provides real-time feedback to the person performing the test on the fluid 24 to assist in quickly determining whether fluid 24 was properly prepared. This feedback can provide pharmacists and caregivers a verification of proper preparation or an alert of an improper preparation. As shown, display device 34 can be integrated within the same body as the processor unit 32. Display device 34 may also be separated from the processor unit 32. For example, in some embodiments display device 32 is part of a bedside system which is separated from processor unit 32. Display device 34 may include any compatible display technology. For example, in some embodiments display device 34 is at least one of a liquid crystal display (LCD) device, a cathode ray tube (CRT) display device, a plasma display panel (PDP), a light emitting diode (LED) display, or other suitable display.

As shown, in some embodiments, display device 34 is configured to display a graphical user interface (GUI) that displays the identity the fluid 24 and/or other relevant information. In some embodiments, a GUI is configured to provide or display the name of an intended patient, the name of a caregiver, the date and time, and the volume of the fluid. In embodiments incorporating a touch-screen display device 34, display device 34 may function as an input device and the GUI may include input regions wherein a user can input data such as the volume of the fluid, and the caregiver's identity. The GUI can also include push button, such as a scan button, whereby a user can initiate a scan of the fluid 24 in a container via an electronically coupled sensor 26.

Sensor 26 and processor unit 32 are operably interconnected via a communication link 38. In some embodiments, communication link 38 comprises a wireless link (e.g., WiFi, Bluetooth®, WiMax, IR, RF, or other known wireless communication approaches). In other embodiments, communication link 38 comprises a direct wired connection (e.g., electrical wire or optical cable). Further, in some embodiments communication link 38 comprises a direct connection across one or more direct lead contacts. Communication link 38 may further include a cable that is coupled to an input interface of processor unit 32. Such input interface may include a USB port or other suitable port. In some embodiments, the sensor 26 is electronically powered via one or more power lines coupled to the direct wired connection.

When the processor unit 32 is electronically coupled to the sensor 26 via a direct-wired or direct-lead connection, the sensor 26 can be electronically coupled to a connector member 36. The connector member 36 can include one or more lead contacts that can establish an electrical connection to the sensor 26. In some embodiments, connector member 36 extends outward from container 22 such that it can be physically accessed from the exterior of container 22. In these instances, a user can connect an electrical cable to the connector member 36 to establish a communication link 38 therebetween. In some embodiments, the wired connection includes a cable that is coupled to an input interface of the processor unit 32. Such an input interface can include a USB port other suitable port. In some embodiments, sensor 26 is electronically powered via one or more power lines of a direct-wired connection.

In other embodiments, sensor 26 is electronically powered via a separate power supply coupled to the container 22 or powered wirelessly. In some embodiments, one or more power sources, such as one or more batteries are coupled to the container 22 and electronically coupled to the sensor 26 to power the sensor 26. In other embodiments, the sensor 26 is powered wirelessly, such as using wireless RFID technology. Examples of sensors 26 incorporating RFID technology are described in United States Patent Application No. 2008/0129475, which was published Jun. 5, 2008, and which is incorporated herein by reference, in its entirety.

In some embodiments, the attachment device 20 comprises a first end 21 to facilitate coupling of attachment device 20 to opening 40 of container 22, and further comprises a second end 23 to facilitate coupling of attachment device 20 to a receptacle 37 of receiving unit 36. Receiving unit 36 is generally provided as a means for receiving and transmitting sensor measurements from the sensor 26 of attachment device 20. Receiving unit 36 further comprises means whereby to transfer sensor measurements from receiving unit 36 to a processing unit 32. In some embodiments, receiving unit 36 is further configured to provide electrical power to the sensor 26. For example, in some embodiments receiving unit 36 comprises an internal power source and contact leads, wherein a portion of the internal power source is transferred to attachment device 20 via the contact leads (not shown). In other embodiments, the receiving unit 36 is powered via an external power supply. Sensor 26 may further be powered by an internal or external power source of attachment device 20.

In some aspects of the present invention, fluid 24 from the container 22 is introduced into attachment device 20 wherein the fluid is directly exposed to the sensor elements 28. Sensor 26 and sensor elements 28 are then able to detect various parameters or characteristics of fluid 24 and communicate this information to processor unit 32 via receiving unit 36 and communication link 38.

Figure 2:
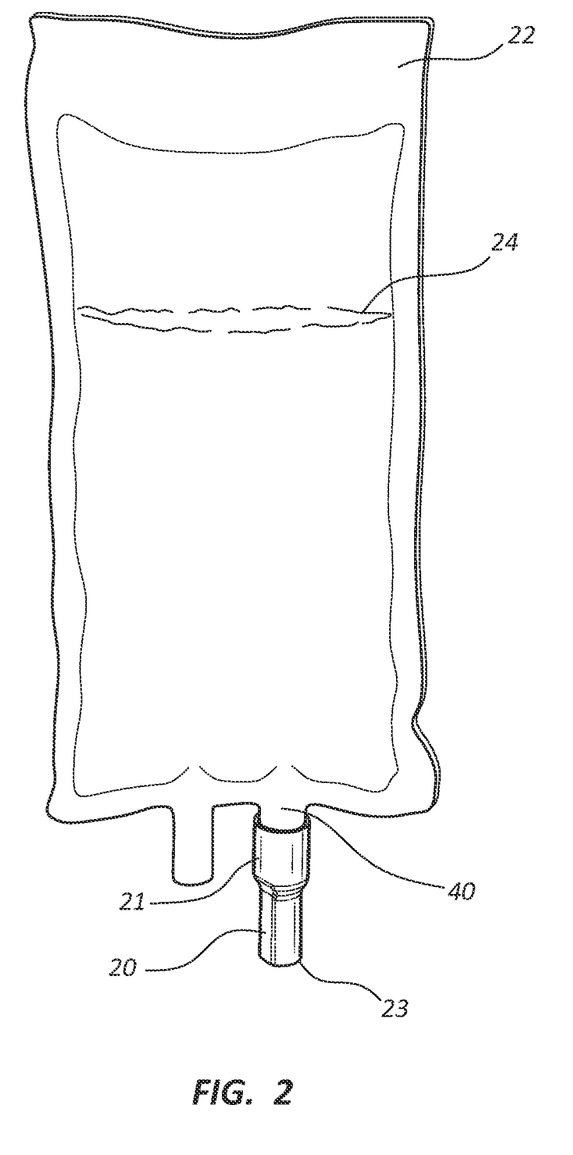
FIG. 2 is a perspective view of an IV bag and an attachment device in accordance with a representative embodiment of the present invention.

Referring now to FIG. 2, attachment device 20 is shown as attached to an IV bag 22. As previously discussed, attachment device 20 may be configured to selectively attach to various types of fluid containers 22. Accordingly, attachment device 20 may be used to test fluids 24 stored in a container. For instance, the attachment device 20 may be configured to attach to a syringe, an IV bag, an ampoule, a vial, an auto-injector container, or other suitable container used to treat a patient. Thus, the first end 21 of attachment device 20 may be shaped and configured to attach to various containers 22.

Attachment device 20 may further be provided as a single-use or multi-use device. Furthermore, it is contemplated that attachment device 20 may be used repeatedly on a single container 22. For example, after a container of fluid 24 is prepared and tested, the attachment device 20 may remain on the container 22 to function as a cap. One or more of the subsequent recipients of the container 22 may leave the attachment device 20 in place and retest the fluid within the container 22 by coupling the attachment device 22 to a processor unit 32. Retesting may be particularly useful and beneficial just prior to drug administration to verify that the correct drug is being administered to the patient. Accordingly, attachment device 20 provides varied and repeated benefits.

Figures 3, 4:
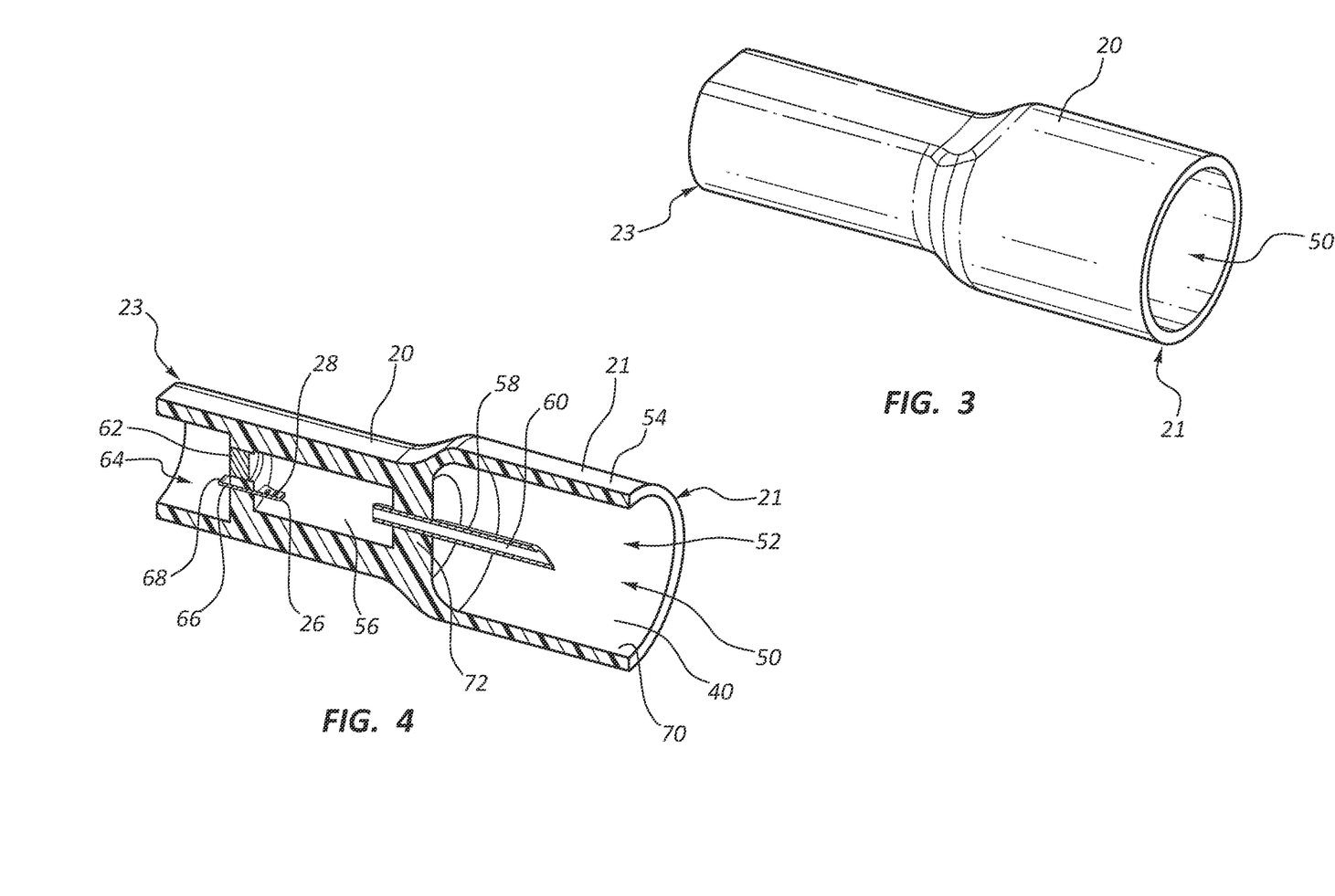
FIG. 3 is a perspective view of an attachment device in accordance with a representative embodiment of the present invention.
FIG. 4 is a cross-section view of the attachment device of FIG. 3.

Referring now to FIGS. 3 and 4, an isolated attachment device 20 is shown. In some embodiments, first and 21 of attachment device 20 is shaped and sized to selectively attach to an opening 40 of container 22. The second end 23 is likewise configured to selectively connect to a processor unit 32 directly, or alternatively connect to the receiving unit 36 which is then directly coupled to a processor unit 32 via a communication link 38. Attachment device 20 further comprises an internal chamber 56 which is defined as a hollow portion of attachment device 20 positioned between first and second ends 21 and 23. Attachment device 20 further comprises a sensor 26 having one or more sensing elements 28 disposed within internal chamber 56. Sensing elements 28 are positioned within internal chamber 56 so as to be in direct contact with a fluid (not shown) present within internal chamber 56.

In some configurations, the first end 21 of attachment device 20 further includes an opening 50 that opens into an inner cavity 52 bound by one or more walls 54. The one or more walls can be shaped and sized to selectively attach to an opening 40 of a container 22. For example, the inner surface 70 of the one or more walls 54 can be shaped and sized to form a press-fit attachment, a locking attachment, a latch attachment, a threaded attachment, or other such attachment with the opening 40 of a container 22. For example, in some embodiments the one or more walls 54 include an attachment feature comprising one or more inner grooves, one or more protrusions, one or more latches, one or more male or female threads, and/or other suitable attachments. In some embodiments, walls 54 consist of a single wall that circumscribes an IV spike 58, wherein the IV spike 58 extends into the cavity 52 in the first end 21 of attachment device 20. Walls 54 may further extend beyond IV spike 58 to shield IV spike 58 and thereby prevent accidental needle sticking. In some configurations, walls 54 are configured to at least partially surround a portion of a container 22, such as an opening 40 or port of container 22. Walls 54 may further comprise features for selectively attaching to an opening 40 or port of container 22.

In some configurations, the second end 23 of the attachment device 20 includes an electrical connector 66 that is configured to operably connect sensor 26 to processor unit 32.

In some embodiments, electrical connector 66 is directly coupled to an input port (not shown) on processor unit 32. In other embodiments, electrical connector 66 is indirectly coupled to processor unit 32 via a communication link 38 and/or receiving unit 36. Electrical connector 66 may include one or more contact surfaces 68 configured to form a direct lead connection with another device, such as a receiving unit 36. When connected to the electrical connector 66, the processor unit 32 can establish and effect electronic communication with the sensor 26. In some embodiments, the electrical connector 66 is disposed on another portion of the attachment body 21 other than the second end 23. For example, in some embodiments electrical connector 66 is disposed on a side or middle portion of attachment device 20.

In some embodiments, internal chamber 56 of attachment device 20 is configured to retain a liquid 24 therein when the first end 21 of attachment device 20 is attached to container 22. Further, in some embodiments internal chamber 56 is configured to retain a liquid 24 follow detachment of attachment device 20 from container 22. As such, the internal chamber 56 can be completely enclosed when the attachment device 20 is attached to the container 22. In some configurations, the internal chamber 56 forms part of the cavity 52 that opens into first end 21 of attachment device 20. In other configurations, internal chamber 56 is separated from the cavity 52 via an internal wall 72. As shown, internal wall 72 may support IV spike 58, wherein fluid path 60 of IV spike 58 provides a means whereby fluid 24 may flow between internal chamber 56 and cavity 52. In other configurations an attachment device 20 is provided that does not include an IV spike 58.

Attachment device 20 may further include a membrane 62. Membrane 62 may be positioned within attachment device 20 between the internal chamber 56 and the external environment. In some embodiments, membrane 62 is permeable to air and impermeable to fluid. As such, when a fluid 24 flows into the internal chamber 56 air is permitted to exit internal chamber 56 via membrane 62, however fluid 24 is prevented from exiting internal chamber 56 into the external environment via membrane 62. Thus, fluid 24 is retained within attachment device 20.

The membrane 62 may include various materials and components that provide these properties. For example, in some embodiments membrane 62 is hydrophobic. In other embodiments the membrane 62 comprises glass, polyethylene terephthalate (PET), a microfiber material, and/or other synthetic material made of high-density polyethylene fibers, such as TYVEK® material from DuPont. Further, in some embodiments membrane 62 comprises a plurality of small holes interposed between internal chamber 56 and replaced with small holes (not shown) that extend between the internal chamber 56 and cavity 64, wherein the small holes comprise sufficient surface areas to permit passage of air, but prevent passage of fluid 24.

Figures 5, 6:
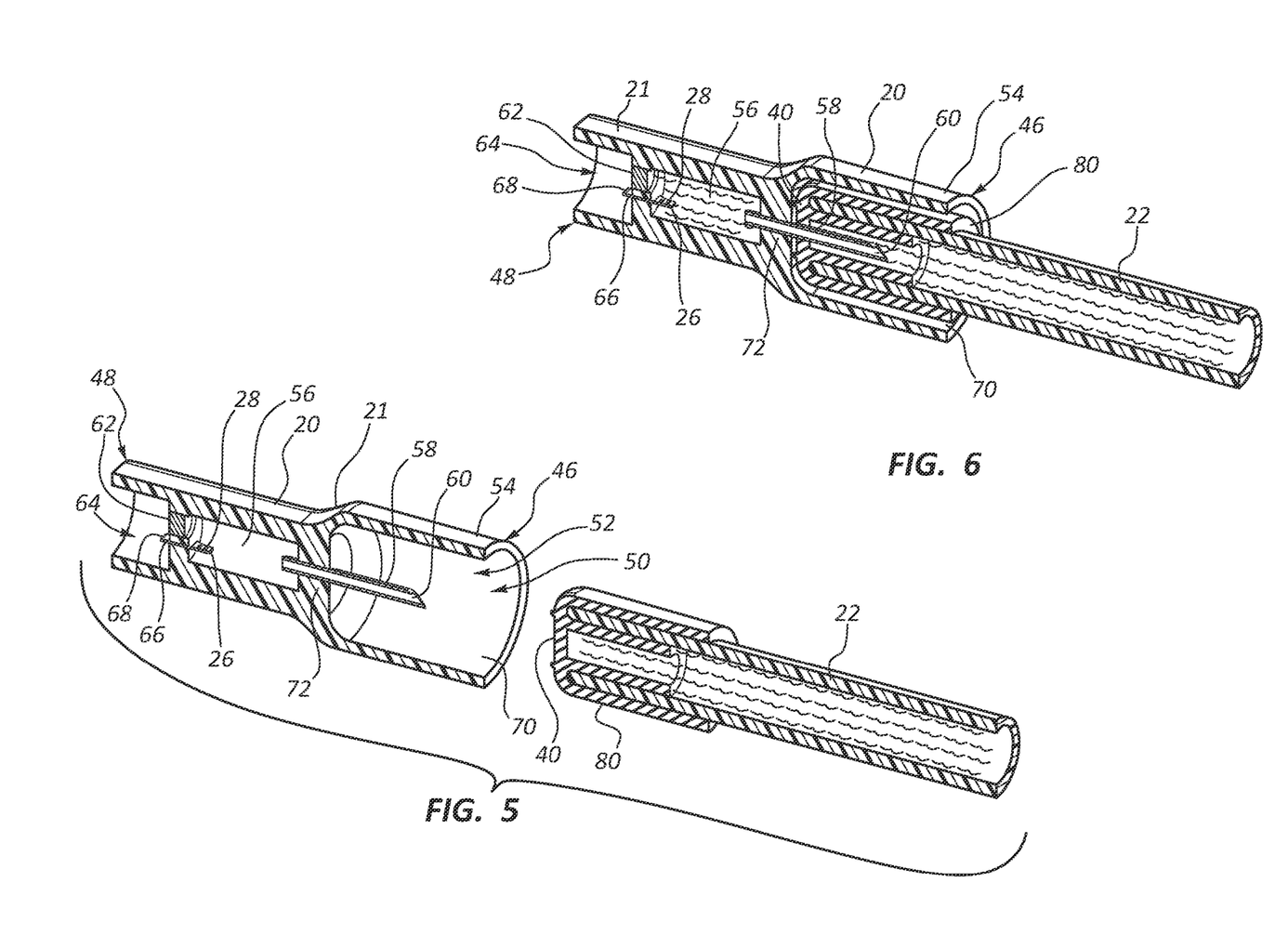
FIG. 5 is a cross-section view of the attachment device of FIG. 3 prior to attachment to a container in accordance with a representative embodiment of the present invention.
FIG. 6 is a cross-section view of the attachment device of FIG. 3 following the attachment to a container in accordance with a representative embodiment of the present invention.

Referring now to FIGS. 5 and 6, an attachment device 20 is shown during use. FIG. 5 shows first end 21 of attachment device 20 approaching opening 40 of container 22. Opening 40 may include a valve portion 80 of an IV bag that is intended to be pierced with an IV spike 58. As previously discussed, portion 80 of container 22 may comprise any and/or size as may be desired to selectively attach container 22 to attachment device 20. As shown, portion 80 is shaped and sized to press-fit within the cavity 52 in the first end 21 of attachment device 20.

FIG. 6 illustrates the attachment device 20 following coupling of container 22. Opening 40 is received by cavity 52 thereby causing IV spike 58 to pierce and provide a pathway through opening 40. After IV spike 58 pierces container 22, a fluid path 60 is opened between the container 22 and the internal chamber 56. As fluid 24 flows into the internal chamber 56, air is expelled from internal chamber 56 via membrane 62. Fluid within internal chamber 56 is in direct contact with sensor elements 28 of the sensor 26 thereby permitting sensor 26 to perform one or more tests on fluid 24. Attachment device 20 is further coupled to processor unit 32 while maintaining the connection between attachment device 20 and container 22. In some embodiments, fluid 24 is retained within internal chamber 56 following removal of attachment device 20 from container 22. As such, fluid 24 may be analyzed by sensor 26 and processor unit 32 following detachment of container 22 from attachment device 20.

In some embodiments, sensor 26 is provided in proximity to fluid 24, wherein sensor 26 is capable of detecting and/or analyzing fluid 24 without contacting fluid 24. For example, sensor 26 may include an optical sensor, such as a photodiode, an image sensor, a thermographic camera, or an optical fiber connection. Accordingly, the identity or other desired characteristics of fluid 24 may be determined by sensor 26 without requiring contact between fluid 24 and sensor 26.

Figure 7:
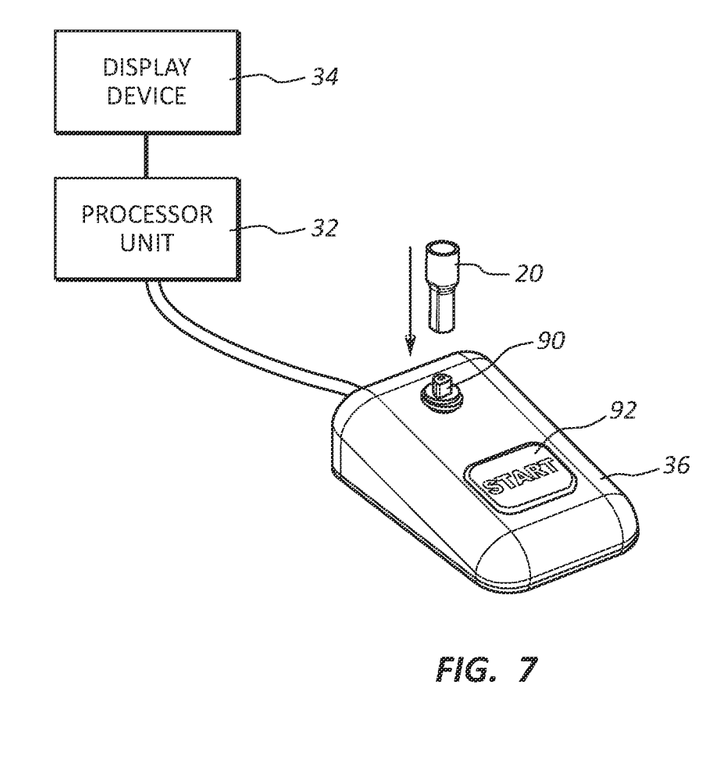
FIG. 7 is a diagrammatic, perspective view of a system for identifying one or more constituents within a fluid in accordance with a representative embodiment of the present invention.
Figure 8:
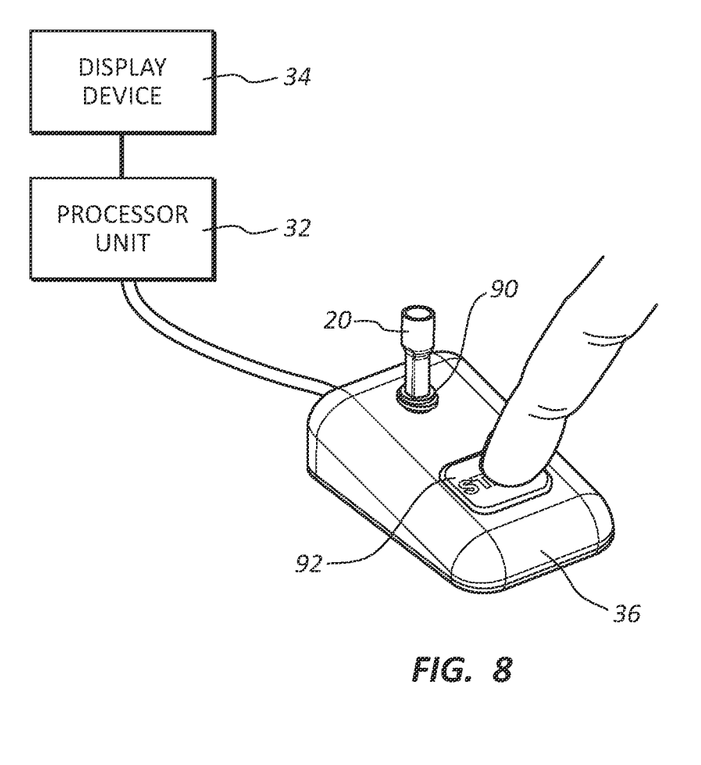
FIG. 8 is a diagrammatic, perspective view of the system of FIG. 7 in accordance with a representative embodiment of the present invention.

Referring now to FIGS. 7 and 8, an attachment device 20 and a receiving unit 36 are shown in accordance with a representative embodiment of the present invention. Some embodiments of the present invention comprise a receiving unit 36 having a start button 92. When actuated, start button 92 causes receiving unit 36 to power sensor 26 within the attachment device 20. Once powered, sensor 26 initiates and performs one or more tests on fluid 24. In some embodiments, attachment device 20 may be further coupled to a container while being coupled to receiving unit 36. Alternatively, the attachment device 20 may be separated from a container 22, as shown, with a portion of fluid 24 from the container 22 remaining within internal chamber 56 of attachment device 20.

Receiving unit 36 may include various means for electronically or otherwise operably coupling to attachment device 20. For instance, in some embodiments receiving unit 36 comprises a protruding connector member 90 that is shaped and sized to enter within the cavity 64 of the second end 23 of attachment device 20. Protruding connector member 90 may have one or more contact surfaces or other such structures (not shown) configured make contact with one or more contact surfaces 68 of attachment device 20 to form an electrical connection.

In some configurations, receiving unit 36, processor unit 32, and display device 34 are individual components of a fluid identification system 30. In other configurations, processor unit 32 and receiving unit 36 from an integral unit operably coupled to a separate display device 34. In still other configurations, processor unit 32, receiving unit 36 and display device 34 form an integral unit. Accordingly, it will be understood that a processor unit 32 can have various configurations.

Figure 9:
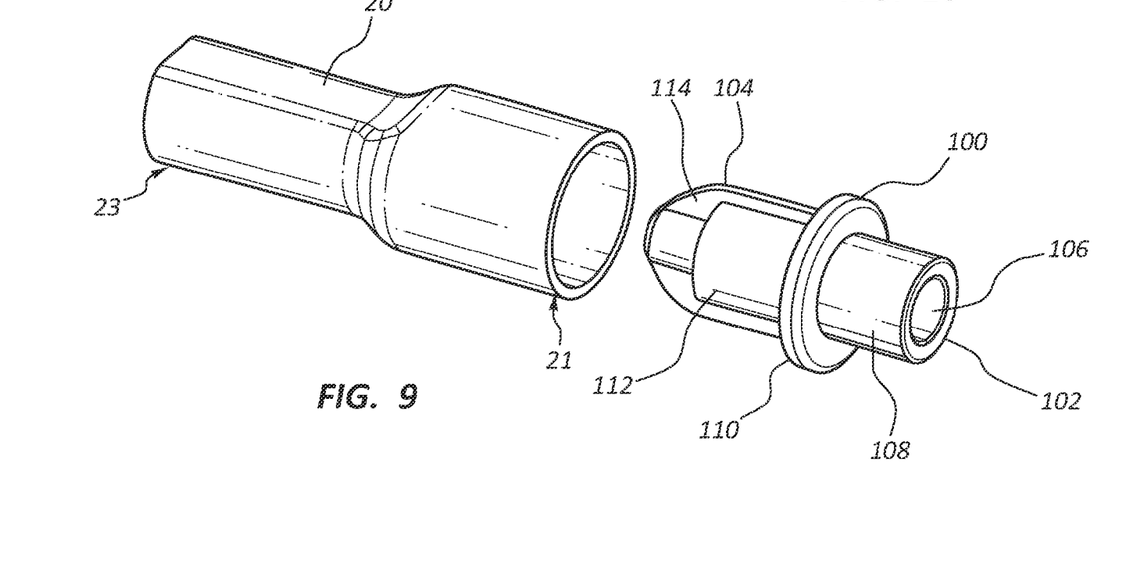
FIG. 9 is a perspective view of an attachment device and an adapter unit in accordance with a representative embodiment of the present invention.
Figure 10:
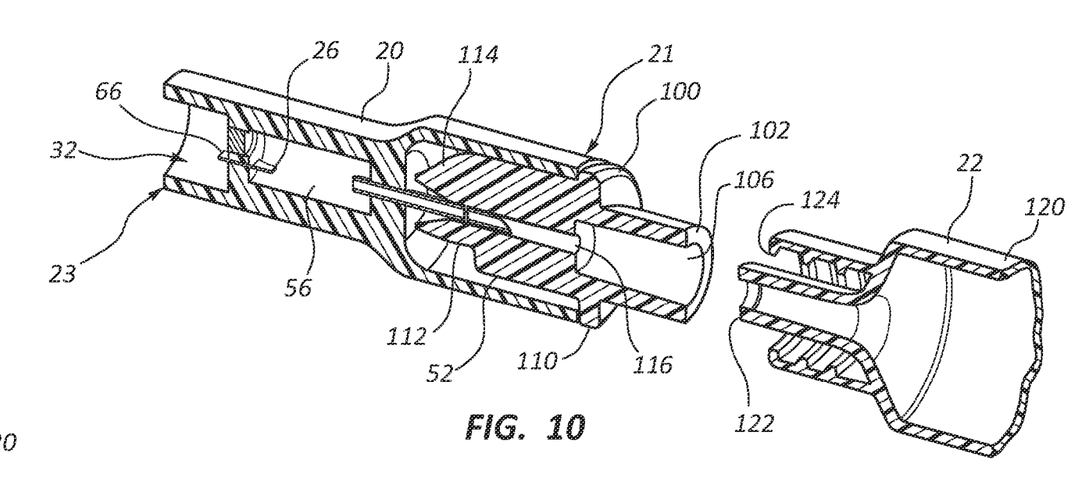
FIG. 10 is a cross section view of the attachment device and adapter unit of FIG. 9 wherein the adapter unit is inserted within the attachment device in accordance with a representative embodiment of the present invention.

Referring now to FIGS. 9 and 10, an attachment adapter 100 and an incompatible container 22 are shown. In some embodiments, the shape or size of first end 21 of attachment device 20 may be incompatible to attach a desire container 22. Accordingly, an attachment adapter 100 may be provided having a first and second end 102 and 104 for compatibly coupling to container 22 and adapter device 20, respectively. The use of an attachment device 20 with or without an attachment adapter 100 may provide a relatively inexpensive and/or disposable device to test a fluid from a variety of containers 22 and container types. By providing one or more attachment adapters 100, attachment device 20 can be attached to many types of IV containers 22.

For example, in some embodiments attachment device 20 is configured to attach to an IV bag. As such, the attachment device 20 comprises an IV spike 58. To enable coupling between attachment device 20 and a syringe 120 with a blunt tip 122, an attachment adapter 100 may be provided.

Attachment adapter 100 may include a first adapter end 102 that attaches to container 22 and a second adapter end 104 that attaches to attachment device 20. In some configurations, second adapter end 104 is shaped and sized to be inserted into a cavity 52 of first end 46 of attachment device 20. Second adapter end 104 further includes an inner passage 116 that receives IV spike 58 to form a fluid path into the IV spike 58. The outer surface 112 of the second adapter end 104 may be shaped and sized to fit within the cavity 52 of the first end 46 of the attachment device 20. This outer surface 112 may further include ribs 114 or other structural features that form an attachment between attachment adapter 100 and attachment device 20, such as a press-fit attachment or a latching attachment. Further still, first adapter end 102 may include an inner surface 106 and/or and outer surface 108 that are shaped, sized and otherwise configured to attach to container 22.

In some embodiments, first adapter end 102 is configured to attach to a syringe 120 having a blunt tip 122. In other embodiments, first adapter end 102 comprises one or more threads (not shown) for coupling with threads 124 of a container 22. In some configurations, an annular ring 110 extends out from the adapter unit 100, separating first adapter end 102 from second adapter end 104 and further forming a barrier that at least partially seals cavity 52 from an exterior environment.

Figure 11:
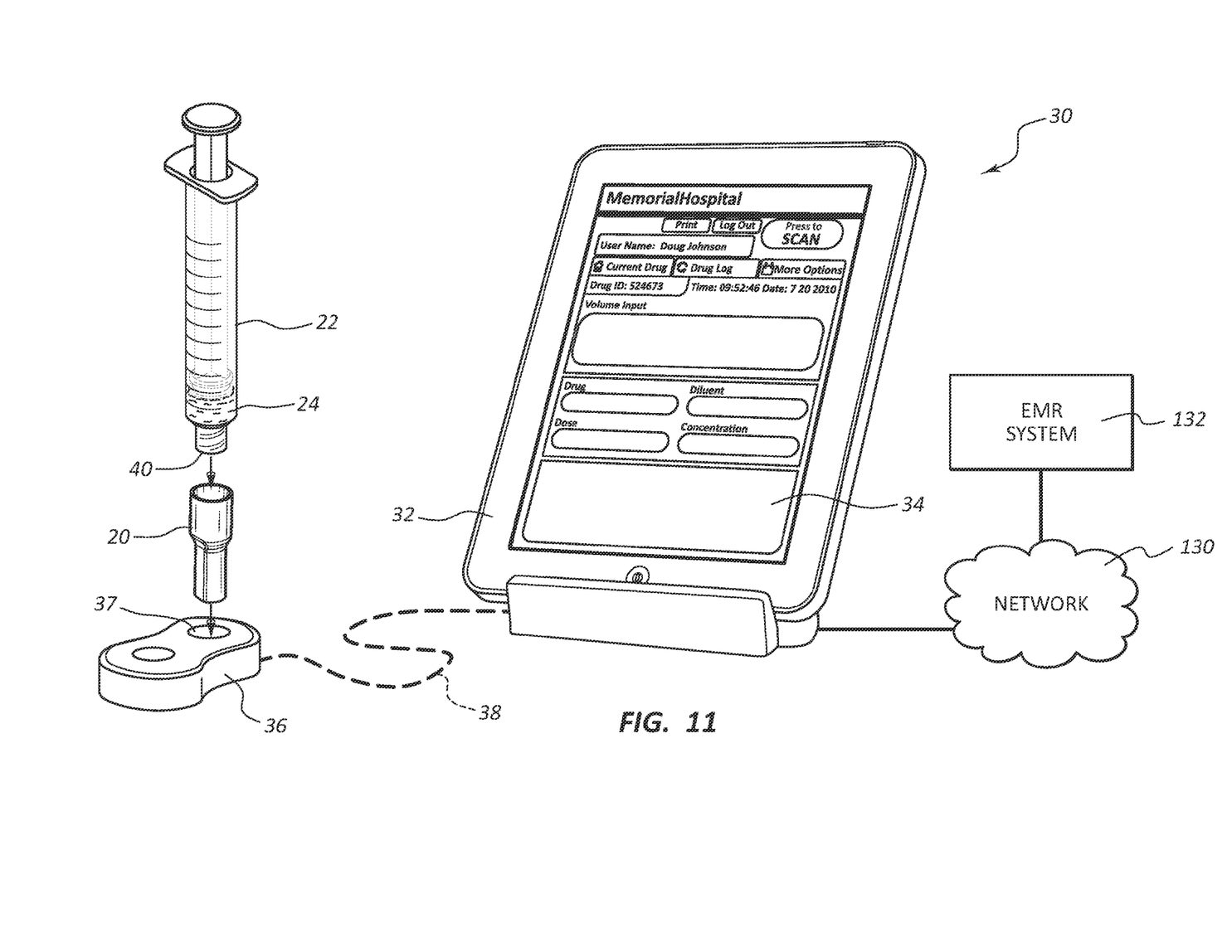
FIG. 11 is a diagrammatic, perspective view of a fluid identification system operably connected to a computer network and an EMR system in accordance with a representative embodiment of the present invention.

Referring now to FIG. 11, a fluid identification system 30 of the present invention is shown as electronically or otherwise operably coupled to a computer network 130, wherein the computer network 130 is further operably coupled to or otherwise includes an EMR system 132. In some configurations, the computer network 130 is a computer network 130 of a hospital or other such care facility. The computer network 130 can be any form of a wide area network (WAN), for example the Internet, or any form of a local area network (LAN), as is understood.

Computer network 130 and processor unit 32 are operably connected such that processor unit 32 is able to receive information from and record information to EMR system 132. An EMR is a computerized medical record for a patient. EMRs are generally provided to record patient treatment information, patient medical history, patient contact information, patient insurance and billing information, and the like. EMR systems 132 of the present invention refer to computer systems that operate one or more sets of EMRs. For instance, a care facility can include one or more EMR systems 132 that operates on plurality of computer devices and/or computer systems. Some EMR systems 132 store medical test results, medical images or scans, and other such records, documents, and findings. An EMR system 132 may further be specific to a care facility, such as a hospital or physician's office.

For example, when a fluid 24 is initially ordered for a patient, the medication order is recorded on EMR system 132 by the ordering physician or other caregiver. When operably connected to computer network 130, processor unit 32 is able to access the medication order stored on EMR system 132. Using this information, processor unit 32 compares the identification of the prescribed fluid with the identification of the prepared fluid 24 as identified by the fluid identification system 30. Additionally, processor unit 32 can record the identified contents and characteristics of the fluid 24 on EMR system 132. This information may be used for record-keeping purposes, for tracking the lifecycle of container 22 and/or fluid 24, for billing a patient for use of the fluid 24, and/or for tracking inventory.

An EMR may further include a subset of records commonly referred to as electronic medication administration records (EMARs). An EMAR can include any type of record for medical care that is generated and stored in electronic form. An EMAR can record medication orders that provide specific instructions on the identity of the fluid 24. These medication orders can provide the processor unit 32 with data by which to compare the identity of the fluid 24 within the container 22. For example, processor unit 32 can access a medication order recorded in the EMAR and compare the identity of the ordered fluid with the identity of the actual fluid 24 within the container 22, as determined by the fluid identification system 30. If the identity of the fluid does not match the medication order, the system 30 can provide an alert to the caregiver. The caregiver can then prepare or order a replacement fluid 24. The processor unit 32 may further require the pharmacist or caregiver to override the alert before completing any subsequent operations on the system.

Processor unit 32 may also be configured to record information to the EMR of the patient for whom the fluid 24 is intended. For instance, processor unit 32 may record the identity of one or more drugs within the fluid 24, the dose of the drugs, the temperature of the drugs, a diluent, and/or other such information. Processor unit 32 may further comprise automatic recording features that may be used to reduce manual recording efforts, improve subsequent billing procedures, and reduce the likelihood of data entry errors.

Figure 12:
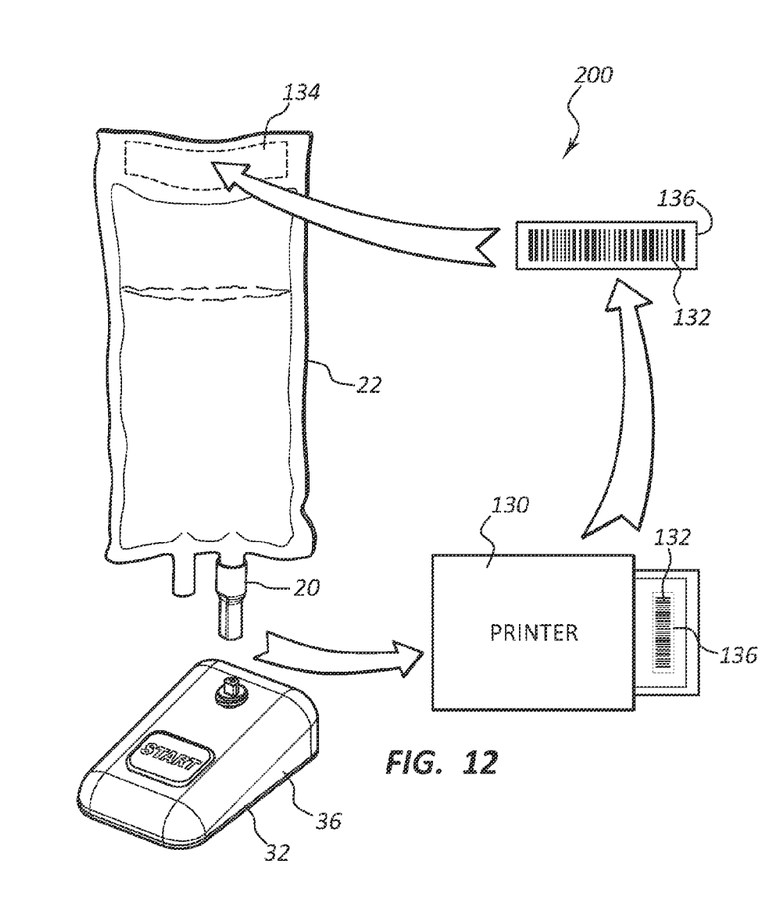
FIG. 12 is a diagrammatic view of a fluid identification system in accordance with a representative embodiment of the present invention.
Figure 13:
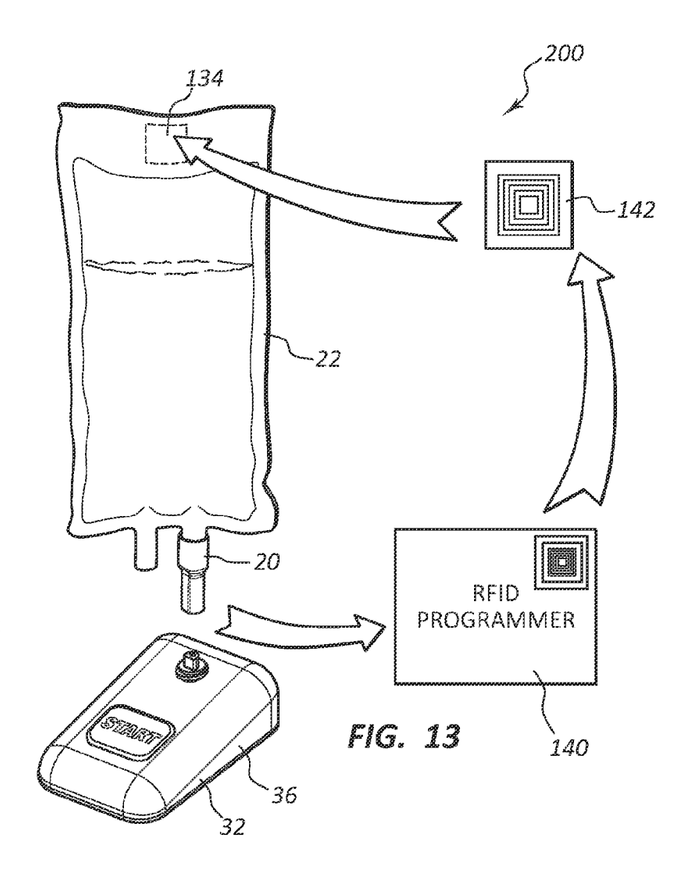
FIG. 13 is a diagrammatic view of a fluid identification system in accordance with a representative embodiment of the present invention.

Referring now to FIGS. 12 and 13, a fluid identification system 200 configured to prepare a label 136, is shown. Following identification of fluid 24 by processor unit 32, this information is displayed to a user via a display device. For instance, when system 200 is used in a pharmacy, the fluid identity can be communicated to the pharmacist or pharmacist technician through a computer screen. The pharmacist can thereby verify that the compounded fluid has the same contents and characteristics as that prescribed by the requesting physician in a medication order.

With reference to FIG. 12, after the identification of the fluid 24 has been verified, system 100 provides a label 136 that may be affixed to a portion 134 of container 22. Label 136 comprises information to indicate the correct and the verified identity of fluid 24. This automated or semi-automated labeling process thereby avoids problems involved with incorrect labeling. In some embodiments, label 136 comprises a barcode 132 or other computer recognizable code which communicates the information to an appropriate reader (not shown), such as those used in some hospitals or other care facilities. Label 136 can also include plain text which is readable by a caregiver. Accordingly, in some embodiments, a printer 130 is electronically coupled to the processor unit 32 and configured to print a label 136 having a barcode 132 or other desired format which includes information related to the identity of fluid 24.

With reference to FIG. 13, processor unit 32 can alternatively or additionally be coupled to an RFID programmer 140. The RFID programmer 140 can program an RFID chip 142 that can be affixed to a portion 134 of container 22 as a label. In some instances, an RFID chip 142 is incorporated into a cap or other enclosure of container 22. RFID chips 142 can transmit information to a computer system having an RFID reader (not shown), such as those included in a treatment facility, such as a hospital or other care facility. The RFID chip 142 can be programmed with information that communicates the identity of the fluid 24. Accordingly, in some embodiments, an RFID programmer 140 is electronically coupled to the processor unit 32 and configured to program an RFID chip 142 with information relating to the identity of the fluid 24.

In some embodiments, a label may also include information related to the patient, such as the patient's name, age, weight, sex, gender, ethnicity, and/or allergies. This information can be obtained from the patient's EMR, as contained in the EMR system 132. Other data may be included on label 132 or RFID chip 142, including the specific contents and characteristics of the fluid 24, a drug lot number, and a drug manufacturer of a drug contained within the fluid 24. Labels may also identify the clinician who prepared the fluid 24, the date and time when the fluid 24 was prepared, and/or the temperature, history, and/or light exposure history of the fluid 24. Once applied to the container 22, the label may be used for subsequent verification by clinicians and caregivers.

When drug preparation and drug identification are performed at an outsourced pharmacy, a label may be scanned to verify the identity of the fluid 24. Alternatively, the outside pharmacy may verify the container's contents using a fluid identification system 30 or 200, as disclosed herein.

In some care facilities, fluids 24 are delivered using an automatic dispensing cabinet (ADC). When delivered through ADCs, a processor unit 32 can be incorporated into the ADC to identify fluid 24 within the container 22 and display this information on a display device 34 of the ADC. Alternatively, if there is a label or RFID chip affixed after a pharmacy scan, the fluid identity can be obtained directly from the label without re-scanning the container's 22 contents using the fluid identification system 30 or 200.

If fluid 24 is stored in a medication room, a processor unit 32 can be located in that area for fluid identification. Alternatively, if a label is affixed to the container 22 from a pharmacy, the nurse may avoid identifying the fluid with a fluid identification system 30 or 200, and simply scan the label to obtain the desired information. Where the system communicates with the patient's EMR, the system 200 may automatically compare the container's 22 contents against the medication order for the patient.

In some embodiments, a fluid identification system 30 or 200 is used by a caregiver prior to administering a fluid 24 to check and verify the identity of the fluid 24 against the fluid's medication order. Where a label is affixed to the container 22 following a pharmacy scan, the caregiver simply obtain the desired information from the label. When the system is used at a patient's bedside, the patient's information can be communicated to clinicians through a display device 34 located on or close to the patient's bedside. Display devices in accordance with the present invention may further be used to access the patient's electronic record from an EMR system 132. Accordingly, the system may also be used to print out a record for the caregiver to verify that the identified drug matches the prescribed medication. When the sensor system 30 or 200 is configured to communicate with the patient's EMR, it may automatically perform a verification of the container's 22 contents against the medication profiled for the patient.

The identification approaches described herein may further include certain notice features (e.g., alarms) to provide notice to a pharmacist, nurse, clinician, or other caregiver that a fluid 24 is incongruous with a prescribed medication order. Such notice can alert the pharmacist or the caregiver of the error so that it may be corrected. In this manner, the present devices, systems, and methods can reduce the likelihood of adverse drug events involving harmful medication errors.

The systems described herein provide a number of useful features. For example, the systems of the present invention accurately identify a fluid 24 thereby enabling clinicians and caregivers to verify that a fluid 24 is correctly prepared at various stages prior to administering the fluid to a patient. Additionally, in some configurations a drug dose and concentration, the identity of a diluent, the temperature of a fluid 24, a flow measurement of a fluid 24, and/or a degradation of a drug within a fluid 24 is identified by the present systems. The system may also automatically synchronize information from the container's 22 contents with a patient's EMR and/or EMAR to verify the identity of the fluid 24 against the medication order, and thereafter automatically record the identity of the fluid 24 in the patient's EMR and/or EMAR. The system can also automatically prepare a label 136 or RFID chip 142 that can be attached to the container 22.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An attachment device for identifying one or more characteristics of a fluid contained within a container to which the attachment device connects, comprising:
   a first end configured to selectively attach to an opening of a container;
   a second end forming an internal chamber;
   a sensor having a sensor element, the sensor element being positioned within the internal chamber, the sensor being configured to perform at least one test to identify one or more characteristics of a fluid within the internal chamber; and
   a spike having a first end positioned within the first end of the attachment device and a second end positioned within the internal chamber, the spike configured to pierce a seal of the container when the container is attached to the first end of the attachment device thereby causing the fluid to flow from the container through the spike and into the internal chamber of the attachment device where the one or more characteristics of the fluid are tested by the sensor.

2. The attachment device of claim 1, wherein the first end further comprises at least one of a cap, a luer adapter, and a stopper.

3. The attachment device of claim 1, wherein the container is at least one of an IV bag, a syringe, an ampule, and a vial.

4. The attachment device of claim 1, wherein the sensor comprises a contact surface externally accessible via the second end of the attachment device.

5. The attachment device of claim 1, further comprising a gas permeable membrane disposed between the internal chamber and an exterior environment that is configured to vent air from within the internal chamber to the exterior environment.

6. The attachment device of claim 1, further comprising an attachment adapter having a first adapter end configured to attach to the first end of the attachment device and a second adapter end configured to attach to the opening of the container.

7. The attachment device of claim 6, wherein the first adapter end comprises an inner passage that receives the spike.

8. The attachment device of claim 1, wherein the sensor is further configured to perform tests on the fluid useful in identifying the concentration, dose, or degradation of one or more drugs in the fluid.

9. The attachment device of claim 1, further comprising an internal wall that separates the internal chamber from a cavity formed by the first end, the spike extending through the internal wall.

10. A system for identifying at least one characteristic of a fluid contained within a container, comprising:
- a first end configured to selectively attach to an opening in a container of fluid;
- a second end forming an internal lumen;
- a sensor having a sensor element positioned within the internal lumen, the sensor being configured to detect at least one characteristic of the fluid;
- a spike having a sharpened tip positioned within the first end and extending into the internal lumen, the spike configured to pierce a seal of the container when the container is attached to the first end thereby causing the fluid to flow from the container through the spike and into the internal lumen where the at least one characteristics of the fluid is detected by the sensor; and
- a processor unit operably connected to the sensor of the attachment device.

11. The system of claim 10, wherein the processor unit is operably connected to the sensor of the attachment device via at least one of a wired and a wireless connection.

12. The system of claim 11, wherein the processor unit is operably connected to an EMAR system.

13. The system of claim 10, further comprising an RFID chip positioned within a cap of the container of fluid, wherein the RFID chip comprises a machine recognizable code that contains the identity of the at least one characteristic of the fluid.

14. A method of identifying one or more constituents within a fluid contained within a container, the method comprising:
attaching an attachment device to an opening of a container having a fluid, the attachment device comprising:
- a first end configured to selectively attach to the opening of the container;
- a second end forming an internal chamber;
- a sensor having a sensor element, the sensor element being positioned within the internal chamber, the sensor being configured to perform at least one test to identify one or more constituents of a fluid within the internal chamber; and
- a spike having a first end positioned within the first end of the attachment device and a second end positioned within the internal chamber, the spike configured to pierce a seal of the container when the container is attached to the first end of the attachment device thereby causing the fluid to flow from the container through the spike and into the internal chamber of the attachment device;

operably connecting the attachment device to a processor unit; and identifying one or more constituents of the fluid contained within the internal chamber using the processor unit, wherein the processor unit processes a sensor measurement from the sensor to identify the one or more constituents of the fluid.

15. The method of claim 14, further comprising a step for displaying the identity of the one or more constituents on a display unit operably connected to the processor unit.

16. The method of claim 14, wherein the processor unit is operably connected to an EMR system, the method further comprising a step whereby the processor unit records the identity of the one or more constituents in the fluid in the EMR system.

17. The method of claim 16, further comprising a step for displaying an identity of the one or more constituents of the fluid.

* * * * *